United States Patent [19]

Erickson

[11] 4,432,986
[45] Feb. 21, 1984

[54] TETRAZOLES BONDED TO CERTAIN POLYCYCLIC AROMATIC SYSTEMS AND ANTI-ALLERGIC USE THEREOF

[75] Inventor: Edward H. Erickson, St. Paul, Minn.

[73] Assignee: Riker Laboratories, Inc., St. Paul, Minn.

[21] Appl. No.: 361,130

[22] Filed: Mar. 23, 1982

Related U.S. Application Data

[63] Continuation-in-part of Ser. No. 49,280, Jun. 18, 1979, abandoned.

[51] Int. Cl.$^3$ .................. C07D 257/02; A61K 31/41
[52] U.S. Cl. .................................... 424/269; 548/252; 548/253
[58] Field of Search ....................... 548/252; 424/269; 543/253

[56] References Cited

U.S. PATENT DOCUMENTS

| | | | |
|---|---|---|---|
| 3,642,997 | 2/1972 | Shen et al. | 424/250 |
| 3,887,574 | 6/1975 | Ellis et al. | 260/308 D |
| 3,905,989 | 9/1975 | Hodson et al. | 260/308 D |
| 3,975,403 | 8/1976 | Gante et al. | 260/327 P |
| 4,145,350 | 3/1979 | Hodson et al. | 260/308 D |
| 4,146,631 | 3/1979 | Ford et al. | 424/269 |
| 4,147,694 | 4/1979 | Erickson | 546/169 |
| 4,232,024 | 11/1980 | Winter et al. | 424/251 |

Primary Examiner—Paul M. Coughlan, Jr.
Assistant Examiner—D. B. Springer
Attorney, Agent, or Firm—Donald M. Sell; James A. Smith; Robert W. Sprague

[57] ABSTRACT

Amides obtained by reaction of aminotetrazole and certain optionally substituted polycyclic aromatic acids are potent anti-allergic agents.

13 Claims, No Drawings

TETRAZOLES BONDED TO CERTAIN POLYCYCLIC AROMATIC SYSTEMS AND ANTI-ALLERGIC USE THEREOF

RELATED APPLICATION DATA

This application is a continuation-in-part of application Ser. No. 49,280, filed June 18, 1979 now abandoned.

TECHNICAL FIELD

This invention relates to physiologically active compounds which are amides obtained by condensing aminotetrazole with certain optionally substituted polycyclic aromatic acids. The invention also relates to anti-allergic compositions containing the compounds and to an anti-allergic method which comprises applying a compound of the invention to a mammalian organism in need thereof.

BACKGROUND ART

The compounds of U.S. Pat. No. 3,887,574 are amides of aminotetrazole and acid-substituted chromones, xanthones and anthraquinones which are anti-allergic agents. The compounds of U.S. Pat. No. 4,145,350 are certain tricyclic compounds which are substituted, inter alia, with a carboxyl group, a carboxylate salt group, an alkyl carboxylate group, a carboxamide group (optionally N-substituted by an alkyl group), a 5-tetrazolyl group, a 5-tetrazolyl salt group, a 5-(1-alkyl)tetrazolyl group, or a 5-(2-alkyl)tetrazolyl group and which are described as anti-allergic agents. The compounds of U.S. Pat. No. 4,147,694 (assigned to the assignee of the present invention) are optionally substituted 8-(1H-tetrazol-5-ylcarbamoyl)quinolines and pharmaceutically acceptable salts thereof, which are also anti-allergic agents. The compounds of U.S. Pat. No. 4,232,024 are certain 1-oxo-1H-pyrimido[6,1-b]-benzthiazole derivatives which are substituted, inter alia, by the moiety COX (where X is hydroxy, alkoxy, or tetrazolyl-5-amino) and which are described as anti-allergic agents.

DISCLOSURE OF INVENTION

The compounds of the present invention can be represented by the formula

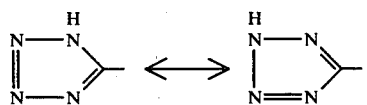

wherein R is hydrogen or lower ($C_{1-4}$) alkyl and Ar is selected from

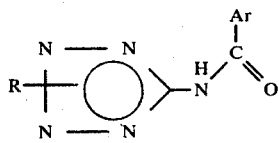

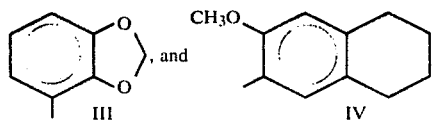

The present invention also provides anti-allergic compositions containing compounds of the invention together with a pharmaceutically acceptable carrier. In addition, the present invention provides a method for inhibiting allergic reactions.

DETAILED DESCRIPTION

In the foregoing formula, the circle in the tetrazole ring signifies a pair of double bonds which, together with the bonds shown, satisfy all of the valences of the ring carbon atom and all but one valence of the 4 ring nitrogen atoms. The remaining nitrogen valence is satisfied by R.

In the compounds of the invention in which the tetrazole ring is unsubstituted, the hydrogen atom exists in tautomeric form on either the $N^1$ or the $N^2$ atoms, i.e.,

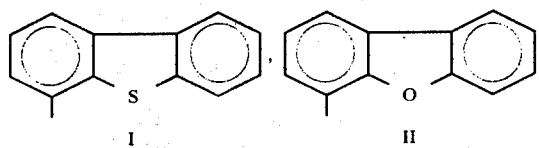

For convenience, however, hydrogen has been depicted herein simply as appearing on the $N^1$ atom. Tautomerism does not occur in the compounds in which the tetrazole ring is substituted with an alkyl group, i.e., the substituent group remains in a single location.

All compounds of the present invention are polycyclic ring systems, and all but compounds of type IV above are heterocyclic ring systems. Compounds of type IV contain an oxygen atom adjacent to the ring, and for the purposes of this specification that oxygen atom will be referred to as a hetero atom. The compounds of the present invention may therefore all be characterized as polycyclic (generally heterocyclic) ring systems in which the carboxamido tetrazole substituent and an oxygen or sulfur hetero atom or ortho on a benzo ring. I have found that ortho positioning of the carboxamido tetrazole substituent and an oxygen or sulfur hetero atom yields an especially potent anti-allergic compound.

Where R is lower alkyl, it is preferably methyl. Preferably R is hydrogen.

The most preferred compounds of the invention have oral activity and are as follows:

N-(tetrazol-5-yl)dibenzothiophene-4-carboxamide,
N-(tetrazol-5-yl)dibenzofuran-4-carboxamide, and
3-methoxy-N-(tetrazol-5-yl)naphthalene-2-carboxamide.

The compounds of the present invention are prepared by reacting the various known acids of the polycyclic aromatic compounds with 5-aminotetrazole or an alkyl 5-aminotetrazole.

It is preferred to prepare the products of this invention through a condensation reaction. Thus, stoichiometrically equivalent amounts of the starting materials (the acid of the polycyclic aromatic compound and 5-aminotetrazole or alkyl 5-aminotetrazole) are dissolved or suspended in a tertiary organic amine, preferably pyridine. A stoichiometric amount of thionyl chloride is added dropwise to the above mixture (if a hydrated form of aminotetrazole starting material is used, then sufficient additional thionyl chloride is added to react with all the water of hydration). During the thionyl chloride addition the mixture is preferably maintained at a temperature of between 40° to 90° C. Other temperatures may be used (depending upon the choice of solvent), and the reflux temperature of the mixture is frequently a convenient temperature.

Alternative methods, involving reactions generally known for the synthesis of amides, may also be used. These methods involve carboxy activation, for example via acid chloride, reaction of the carboxylic acid group with N,N'-carbonyl diimidazole, reaction with N,N'-dicyclohexyl carbodiimide to provide the activated adduct, reaction with ethyl chloroformate, n-butyl chloroformate and the like to provide a mixed anhydride, reaction with p-nitrophenoxybenzyl chloride to provide p-nitrophenoxybenzyl ester, and the like. These methods are generally more complex and expensive, and are only used when the method of choice is unsatisfactory.

If it is desired to prepare a (2-methyl-tetrazol-5-yl)benzamide, the synthetic route may involve reaction of the acid of the polycyclic aromatic compound with 5-amino-2-methyl-tetrazole, or alternatively may proceed via reaction of the acid of the polycyclic aromatic compound with 5-aminotetrazole followed by methylation of the tetrazole ring. Suitable methylating agents for the latter route are methyl bromide and methyl iodide. Methylation will generally result in a mixture of $N^1$ and $N^2$ substituted compounds. Separation may be carried out by crystallization or chromatography.

In order to prepare the compound 3-methoxy-N-(tetrazol-5-yl)naphthalene-2-carboxamide, the compound 3-hydroxy-2-naphthoic acid is alkylated. The alkylation of the acid is carried out with methyl iodide in the presence of a weak inorganic base such as potassium carbonate in a highly polar organic solvent (preferably N,N-dimethylformamide) at moderate temperatures (from about 0° to about 100° C.), then hydrolyzed by heating in a lower alkanol such as ethanol in the presence of a base such as sodium hydroxide.

The compounds of the invention have been shown to inhibit the release, and/or synthesis, and/or effect of biochemical products resulting from the combination of certain types of antibody and specific antigen. Both subjective and objective changes which result from the inhibition of specific antigen by sensitized subjects may be markedly inhibited by administration of the new compounds. The new compounds are useful in the treatment of so-called "intrinsic" asthma (in which no sensitivity to extrinsic antigen can be demonstrated) or any other condition in which non-specific factors trigger the release of allergic mediators; as well as in the treatment of other conditions in which specific antigen-antibody reactions are responsible for disease, for example extrinsic asthma, food allergies, allergic rhinitis, allergic conjunctivitis, atopic dermatitis, hay fever, urticaria and auto-immune diseases.

The compositions of the invention normally contain a compound of the invention (as active ingredient) in association with a pharmaceutically acceptable carrier or diluent. The nature of the composition and the carrier or diluent will depend upon the desired mode of administration, which may be, for example, orally, by inhalation (orally or nasally), parenterally (as by intradermal or intravenous injection) or by topical application. The compositions can be formulated in the conventional manner with conventional ingredients, e.g., they can be put up as solutions, suspensions, syrups, dry powders, tablets or, when intended for topical application, as creams, lotions, or pastes. The compositions of the invention generally contain a minor proportion of the active ingredient and a major proportion of carrier or diluent.

For administration by inhalation, the compounds of the invention (optionally in the form of a salt such as the sodium salt) are dissolved or suspended in water and can be applied by means of a conventional nebulizer. However, the administration of medicaments by means of a pressurized dispensing container, i.e., an aerosol dispenser, is an alternative to nebulizer administration. Aqueous solutions for administration by means of a conventional nebulizer can contain up to about 10 percent by weight of the active ingredient in sterile water; and compositions for dispensing from a pressurized container containing suspensions or solutions of active ingredient in liquified propellants normally contain about 0.2 to 5 percent by weight of the active ingredient.

For administration from an aerosol dispenser, the active ingredient is dissolved or suspended in a liquified propellant medium. Suitable propellants are those conveniently used in formulations for dispensing from pressurized containers, for example, of the halogenated hydrocarbon type such as fluoro- or fluorohalohydrocarbons and mixtures of any of these together with other propellants (see U.S. Pat. No. 2,868,691). Preferred propellants of low toxicity are difluorodichloromethane, dichlorotetrafluoroethane and mixtures thereof. Where the medicament is not soluble in the propellant, it may be necessary to add a surface-active agent to the composition in order to suspend the medicament in the propellant medium. The use of such surface-active agents and the advantages which stem therefrom are more fully described in British Patent Specification No. 1,063,512.

When put up as powders, the compositions of the invention can be administered by means of a conventional insufflator device. In order to improve the properties of the powder for this purpose it is useful to modify the surface characteristics of the powder particles, for example, by coating them with a pharmaceutically acceptable material such as sodium stearate. In addition, finely divided powders containing the active ingredient can be mixed with a coarser diluent material, such as lactose, which may be present in a smaller, equal or greater amount than the amount of active ingredient, for example, in from 50 to 150 percent by weight based on the weight of the active ingredient of the invention and such other pharmaceutically active ingredients as may be present.

The compounds of the invention can also be administered by dispensers from which metered amounts of the compound are discharged in a state to be orally or nasally received during inhalation, wherein the propellant is compressed air or any other compressed inert gas such as nitrogen, argon and the like.

As noted previously, the compounds of the invention are indicated for use in inhibiting the effects of antibody-antigen reactions. The treatment regimen may require repeated dosages of the compound at regular intervals. The amount of compound and frequency of administration will depend upon many factors, and no concise dosage rate or regimen can be generally stated.

However, as a general guide, where the compounds are administered by inhalation to a patient suffering from acute allergic asthma, therapeutically useful results may be achieved when doses of 0.1 to 20 mg/kg are used. When the compounds are administered by oral routes, larger dosages are normally given. The invention thus provides a method for inhibiting the effects of an antibody-antigen reaction by applying to the known or expected site of the antibody reaction a therapeutically effective amount of a compound of the invention.

The compounds of the invention can also be used in the treatment of allergic eye conditions, for example, those associated with hay fever, i.e., allergic conjunctivitis. For such use the compounds of the invention can be used in the form of eye drops and/or spray as an isotonic aqueous solution containing about two percent of the compound and a preservative.

Other active ingredients can also be present in the compositions of the invention. Thus, in compositions for administration by inhalation, it can be beneficial to include a bronchodilator such as isoprenaline, adrenaline, carbuterol, rimiterol, orciprenaline, isoetharine, or derivatives thereof, particularly salts. The amount of bronchodilator used will vary over a broad range, depending, inter alia, upon the nature and activity of the bronchodilator and the compound of the present invention which is used. However, the use of a minor proportion (i.e., less than 50 percent by weight) of the bronchodilator together with from 0.1 to 10 percent by weight of a compound of the present invention is preferred. Such compositions constitute an additional aspect of the invention.

The effectiveness of the compounds of the invention is evaluated by inhibiting passive cutaneous anaphylaxis in a standard test method substantially as described in "Immunology", 16, 749 (1969). The variation of the method generally used is as follows: Sprague-Dawley rats (male or female) having a body weight of about 200 grams are injected intramuscularly with egg albumin and intraperitoneally with *Bordetella pertussis* vaccine. Ten to twelve days after this treatment the rats are exsanguinated via the abdominal aorta to recover the blood, which is allowed to clot overnight. The blood samples are centrifuged in order to remove the blood serum containing the antibody.

This antibody is used in the following way: Sprague-Dawley rats weighing from 50 to 120 grams are sensitized by intradermal injection of 0.1 ml. of antibody-containing serum into the mid-dorsal region. Sensitivity is allowed to develop for 24 hours, and the test compounds are administered (either orally or by intraperitoneal injection) at dose levels selected to provide a range of inhibition values (suitable screening doses are 50, 25, 10 or 5 mg/kg). Six rats are used for each concentration of the compound under test. At various times thereafter (e.g., five minutes), the rats are then injected intravenously with an antigen which contains 1 ml. of a mixture of egg albumin (0.5 mg/ml), Evans Blue dye solution (10 mg/ml), and physiological saline. Six rats are also used as controls for each test, the control rats being injected with the antibody and the antigen in the same way as the test rats but receiving no test compounds. Forty-five minutes after injection of the egg albumin the rats are killed and the skins removed and reversed. The intensity of the anaphylactic reaction is assessed by measuring the area of the characteristic blue weal produced by spread of the Evans Blue dye from the sensitization site, with this area being determined approximately by taking the product of two diameters of the dyed area at right angles to one another. The greater the anaphylactic reaction, the larger is the area of the blue weal. Percent inhibitions are calculated using the formula $$\frac{(\text{Control Group Area} - \text{Treated Group Area}) \times 100}{\text{Control Group Area}}$$

and those values are plotted graphically for each compound so that the dosage required to achieve a 50 percent inhibition of the anaphlactic reaction can be determined. The compounds of the invention are active in this test at non-toxic doses, and exhibit percent inhibition of 30 percent or greater at a 5 mg. oral or intraperitoneal dose. The compounds of the invention of Example Nos. 1-4 exhibit 83, 77, -11, and 52 percent inhibition, respectively, in the above test at a 5 mg. oral dose, and 65, 76, 100, and 98 percent inhibition, respectively, in the above test at a 5 mg. intraperitoneal dose.

The following examples are provided for the purpose of further illustrating the invention but are not intended to limit the scope thereof in any way.

EXAMPLE 1

To a solution of 0.0068 mole of dibenzothiophene-4-carboxylic acid and 0.008 mole of 5-aminotetrazole monohydrate in 20 ml. of pyridine was added 1.3 ml. of thionyl chloride. After stirring for a few minutes, the solid product was separated by filtration, dried and recrystallized from methoxyethanol. The white solid product was N-(tetrazol-5-yl)dibenzothiophene-4-carboxamide (a type I compound), m.p. 288°-289° C.

| Analysis | % C | % H | % N |
|---|---|---|---|
| Calculated for $C_{14}H_9N_5OS$ | 56.9 | 3.05 | 23.7 |
| Found | 56.2 | 3.0 | 24.2 |

EXAMPLES 2-3

Using the method of Example 1 the following compounds of the invention were prepared from the starting materials listed in the table.

TABLE I

| Ex. No. | Starting Material | Product (m.p. °C.) | Compound Type |
|---|---|---|---|
| 2 | | 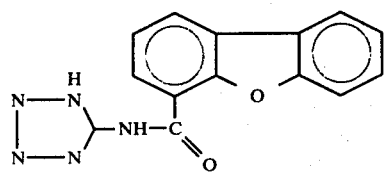 m.p. 284-285° C. | II |

TABLE I-continued

| Ex. No. | Starting Material | Product (m.p. °C.) | Compound Type |
|---|---|---|---|
| 3 | 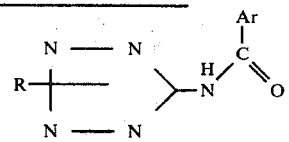 COOH | 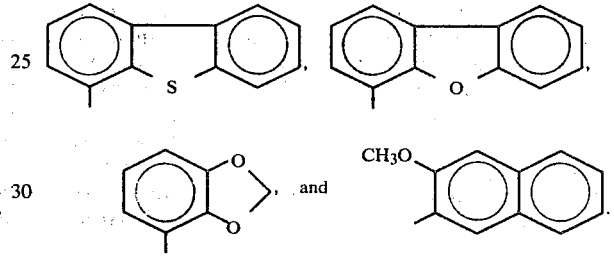 m.p. 240–242°C. | III |

EXAMPLE 4

A mixture of 18.8 g. (0.1 mole) of 3-hydroxy-2-naphthoic acid, 20 ml. of methyl iodide, 28 g. of potassium carbonate, and 200 ml. of N,N-dimethylformamide was heated at 70° C. for 16 hours, then poured into 1 liter of water. The mixture was extracted with diethyl ether and the extracts were washed with water, then 5 percent sodium hydroxide solution, then water again, and dried over magnesium sulfate. Evaporation provided a residue of methyl 3-methoxy-2-naphthoate.

The methyl 3-methoxy-2-naphthoate was diluted with excess 5 percent sodium hydroxide solution and the mixture was heated at its reflux temperature until the solution was clear. The solution was acidified with hydrochloric acid to provide a precipitate which was separated by filtration. Recrystallization from benzene provided the known intermediate 3-methoxy-2-naphthoic acid, m.p. 130°–132° C.

To a mixture of 8.2 g. of 3-methoxy-2-naphthoic acid, 5.2 g. of aminotetrazole, and 80 ml. of pyridine was added dropwise 6.4 ml. of thionyl chloride, maintaining the temperature below 70° C. After stirring for one hour, the mixture was cooled to 25° C. and evaporated to dryness. The residue was washed with dilute hydrochloric acid, then recrystallized from N,N-dimethylformamide, then dissolved in base, filtered, reprecipitated with dilute acid, filtered, washed with methanol, then recrystallized again from N,N-dimethylformamide to provide 3-methoxy-N-(tetrazol-5-yl)naphthalene-2-carboxamide (a type IV compound), m.p. 280°–283° C.

| Analysis | % C | % H | % N |
|---|---|---|---|
| Calculated for $C_{13}H_{11}N_5O_2$ | 58.0 | 4.1 | 26.0 |
| Found | 57.7 | 4.0 | 26.0 |

Various modifications and alterations of this invention will be apparent to those skilled in the art without departing from the scope and spirit of this invention and the latter should not be restricted to that set forth herein for illustrative purposes.

What is claimed is:
1. A compound of the formula wherein R is hydrogen or lower ($C_{1-4}$) alkyl and Ar is selected from

2. Compounds according to claim 1, wherein R is hydrogen.
3. The compound N-(tetrazol-5-yl)dibenzothiophene-4-carboxamide according to claim 2.
4. The compound N-(tetrazol-5-yl)dibenzofuran-4-carboxamide according to claim 2.
5. The compound 3-methoxy-N-(tetrazol-5-yl)naphthalene-2-carboxamide according to claim 2.
6. A compound according to claim 1, wherein R is lower alkyl.
7. A compound according to claim 1, wherein R is methyl.
8. An anti-allergic composition, comprising an effective amount of a compound according to claim 1 and a pharmaceutically acceptable carrier.
9. Compositions according to claim 8, wherein said compound is selected from the group consisting of:
   N-(tetrazol-5-yl)dibenzothiophene-4-carboxamide,
   N-(tetrazol-5-yl)dibenzofuran-4-carboxamide, and
   3-methoxy-N-(tetrazol-5-yl)naphthalene-2-carboxamide.
10. A method for inhibiting asthmatic reactions in a mammal which comprises administering to said mammal a pharmaceutically effective amount of at least one composition according to claim 8.
11. A method according to claim 10, wherein the method of administration is by inhalation.
12. A method according to claim 10, wherein the method of administration is oral.
13. A method according to claim 10, in which said compound is selected from the group consisting of:
   N-(tetrazol-5-yl)dibenzothiophene-4-carboxamide,
   N-(tetrazol-5-yl)dibenzofuran-4-carboxamide, and
   3-methoxy-N-(tetrazol-5-yl)naphthalene-2-carboxamide.

* * * * *

UNITED STATES PATENT AND TRADEMARK OFFICE
CERTIFICATE OF CORRECTION

PATENT NO. : 4,432,986

DATED : February 21, 1984

INVENTOR(S) : Edward H. Erickson

It is certified that error appears in the above-identified patent and that said Letters Patent is hereby corrected as shown below:

Col. 1, line 39, "guinolines" should read --quinolines--.

Col. 2, formula IV, " 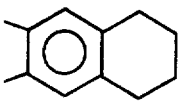 " should read

-- 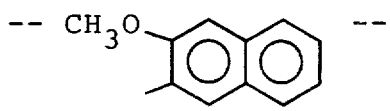 --

Col. 2, line 45, second appearing "or" should read --are--.

Col. 6, Table I, " 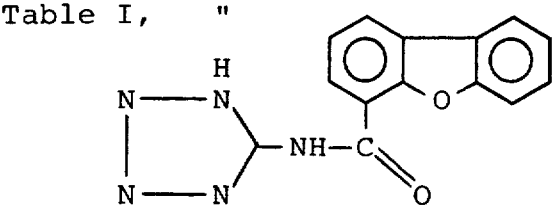 " should read

-- 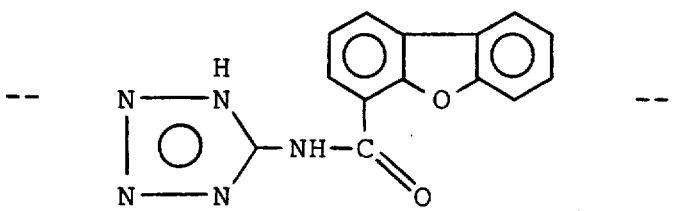 --

UNITED STATES PATENT AND TRADEMARK OFFICE
CERTIFICATE OF CORRECTION

PATENT NO. : 4,432,986   Page 2 of 3
DATED : February 21, 1984
INVENTOR(S) : Edward H. Erickson It is certified that error appears in the above-identified patent and that said Letters Patent is hereby corrected as shown below:

Cols. 7 and 8, Table I, " 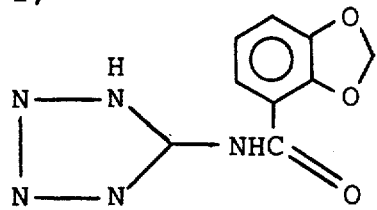 " should read

-- 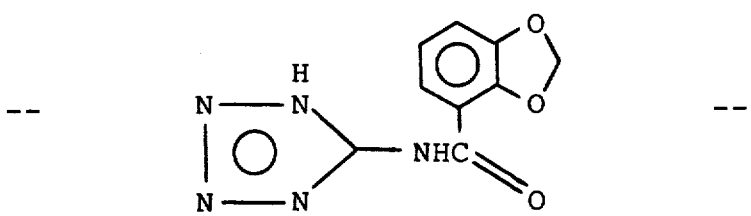 --

UNITED STATES PATENT AND TRADEMARK OFFICE
CERTIFICATE OF CORRECTION

PATENT NO. : 4,432,986

DATED : February 21, 1984

INVENTOR(S) : Edward H. Erickson

It is certified that error appears in the above-identified patent and that said Letters Patent is hereby corrected as shown below:

Col. 8, line 15, " 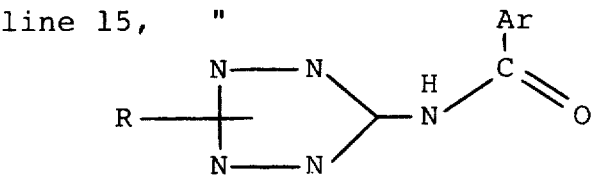 " should read

-- 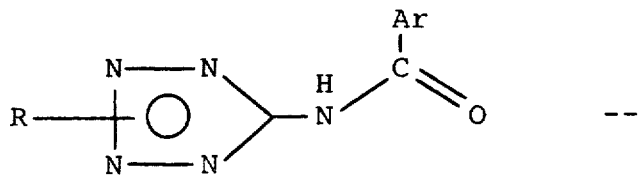 --

Signed and Sealed this

*Fifth* Day of *June 1984*

[SEAL]

*Attest:*

*Attesting Officer*

GERALD J. MOSSINGHOFF

*Commissioner of Patents and Trademarks*